(12) United States Patent
Weis

(10) Patent No.: US 11,324,246 B1
(45) Date of Patent: May 10, 2022

(54) NUTRACEUTICAL DIETARY SUPPLEMENT

(71) Applicant: Michael Bowditch Weis, Waimea, HI (US)

(72) Inventor: Michael Bowditch Weis, Waimea, HI (US)

( * ) Notice: Subject to any disclaimer, the term of this patent is extended or adjusted under 35 U.S.C. 154(b) by 0 days.

(21) Appl. No.: 17/171,779

(22) Filed: Feb. 9, 2021

Related U.S. Application Data

(60) Provisional application No. 62/993,204, filed on Mar. 23, 2020.

(51) Int. Cl.

| | | |
|---|---|---|
| *A23L 33/00* | (2016.01) | |
| *A61K 31/122* | (2006.01) | |
| *A61K 31/728* | (2006.01) | |
| *A61K 38/01* | (2006.01) | |
| *A61K 36/324* | (2006.01) | |
| *A23L 33/17* | (2016.01) | |
| *A61K 36/76* | (2006.01) | |
| *A61K 36/67* | (2006.01) | |
| *A61K 36/74* | (2006.01) | |
| *A23L 33/105* | (2016.01) | |
| *A23L 29/00* | (2016.01) | |
| *A61K 36/9066* | (2006.01) | |

(52) U.S. Cl.
CPC .............. *A23L 33/30* (2016.08); *A23L 29/035* (2016.08); *A23L 33/105* (2016.08); *A23L 33/17* (2016.08); *A61K 31/122* (2013.01); *A61K 31/728* (2013.01); *A61K 36/324* (2013.01); *A61K 36/67* (2013.01); *A61K 36/74* (2013.01); *A61K 36/76* (2013.01); *A61K 36/9066* (2013.01); *A61K 38/014* (2013.01)

(58) Field of Classification Search
CPC ........ A23L 33/30; A23L 29/035; A23L 33/17; A23L 33/105; A61K 31/122; A61K 31/728; A61K 36/324; A61K 36/67; A61K 36/74; A61K 36/9066; A61K 38/014

See application file for complete search history.

(56) References Cited

U.S. PATENT DOCUMENTS

2018/0064779 A1* 3/2018 Jia ...................... A61K 31/737

* cited by examiner

*Primary Examiner* — Aaron J Kosar
(74) *Attorney, Agent, or Firm* — Plager Schack LLP; Mark H. Plager; Kara Verryt

(57) ABSTRACT

A nutraceutical dietary supplement formulation for the treatment of joint pain and discomfort may include astaxanthin powder; *boswellia* serrate gum resin extract; hyaluronic acid; undenatured type II (UC-II) collagen; eggshell membrane collagen powder; turmeric root extract; white willow bark extract; cayenne pepper extract; and Cat's Claw bark powder. The formulation may be formed into capsules for delivery to a user, wherein a therapeutically effective dosage of the formulation may be included in each capsule.

5 Claims, No Drawings

NUTRACEUTICAL DIETARY SUPPLEMENT

RELATED APPLICATION

This application claims priority to provisional patent application U.S. Ser. No. 62/993,204 filed on Mar. 23, 2020, the entire contents of which is herein incorporated by reference.

BACKGROUND

The embodiments herein relate generally to dietary supplements, and more particularly, to a nutraceutical dietary supplement formula for the treatment of joint pain and discomfort.

Millions of Americans suffer from joint pain, osteoarthritis, joint stiffness, and discomfort. Current products for the treatment of joint pain and discomfort contain between 1 and 4 ingredients—mostly well-known, but controversial products, such as methylsulfonylmethane (MSM), chondroitin, and glucosamine. These ingredients, while popular, have not been proven to show any benefits better than a placebo and, in some studies, have been shown to have negative side effects. In other words, the existing formulations do not have enough effective ingredients in a sufficient quantity to be effective in a wide range of patients.

Therefore, what is needed is a nutraceutical dietary supplement formulation comprising a combination of ingredients that are not only safe, but also provide an effective matrix of joint pain and stiffness relief.

SUMMARY

Some embodiments of the present disclosure include a nutraceutical dietary supplement formulation for the treatment of joint pain and discomfort. The formulation may include astaxanthin powder; *boswellia* serrate gum resin extract; hyaluronic acid; undenatured type II (UC-II) collagen; eggshell membrane collagen powder; turmeric root extract; white willow bark extract; cayenne pepper extract; and Cat's Claw bark powder. The formulation may be formed into capsules for delivery to a user, wherein a therapeutically effective dosage of the formulation may be included in each capsule.

DETAILED DESCRIPTION OF CERTAIN EMBODIMENTS

In the following detailed description of the invention, numerous details, examples, and embodiments of the invention are described. However, it will be clear and apparent to one skilled in the art that the invention is not limited to the embodiments set forth and that the invention can be adapted for any of several applications.

The formulation of the present disclosure may be used as a dietary supplement for pain relief and may comprise the following elements. This list of possible constituent elements is intended to be exemplary only, and it is not intended that this list be used to limit the formulation of the present application to just these elements. Persons having ordinary skill in the art relevant to the present disclosure may understand there to be equivalent elements that may be substituted within the present disclosure without changing the essential function or operation of the formulation.

The various elements of the formulation of the present disclosure may be related in the following exemplary fashion. It is not intended to limit the scope or nature of the relationships between the various elements and the following examples are presented as illustrative examples only.

By way of example, some embodiments of the present disclosure include a nutraceutical dietary supplement formulation comprising astaxanthin powder, such as astaxanthin powder 2.5% SCE, *boswellia* serrate gum resin extract, hyaluronic acid, undenatured type II (UC-II) collagen, eggshell membrane collagen powder, such as type IV eggshell collagen, turmeric root extract, such as turmeric root extract 95% curcuminoids, white willow bark extract, cayenne pepper extract, and Cat's Claw bark powder. In embodiments, the formulation may further comprise rice flour and magnesium stearate.

A particular embodiment of the formulation of the present disclosure may comprise about 1 to about 6 mg, such as about 2 mg, astaxanthin powder 2.5% SCE; about 100 to about 200 mg, such as about 150 mg *boswellia* serrate gum resin extract; about 30 to about 50 mg, such as about 42 mg, hyaluronic acid; about 30 to about 50 mg, such as about 42 mg, UC-II collagen; about 75 to about 125 mg, such as about 105 mg, type IV eggshell membrane collagen powder; about 75 to about 125 mg, such as about 104 mg, turmeric root extract; about 25 to about 75 mg, such as about 50 mg, white willow bark extract; about 25 to about 75 mg, such as about 50 mg cayenne extract, and about 75 to about 125 mg, such as about 100 mg, Cat's Claw bark powder.

In embodiments, the ingredients may be combined in the appropriate volumes and delivered in, for example, size 00 vegetable capsules, wherein the recommended dosage may be 2 capsules per day. The average capsule weight may be from about 475 to about 525 mg, such as about 509 mg. The capsule may disintegrate in under 30 minutes, such as within about 11 minutes.

Astaxanthin is a naturally occurring carotenoid algae found in nature commonly consumed by marine animals, wherein the green microalgae Haematococcus pluvialis is considered the richest source of astaxanthin. Carotenoids provide beneficial mechanisms of action for cancers, cardiovascular disease, age-related macular degeneration, and cataract formation. The use of astaxanthin as a potent antioxidant may be beneficial in decreasing the risks of certain chronic diseases while also reducing oxidative stress in the nervous system, thus reducing the risk of neurodegenerative diseases. Moreover, astaxanthin has anti-inflammatory and immune-stimulating effects that have significant implications in degenerative bone and joint disease and the treatment of osteoarthritis and general joint pain.

*Boswellia serrata* may help curb discomfort by moderating the body's natural inflammatory responses. Certain types of *boswellia* may provide joint relief within 5 to 7 days and may help ease discomfort in osteoarthritis patients.

Hyaluronic acid is found in the synovial fluid of joints. This fluid lubricates joints, decreasing friction during movement, which minimizes the likelihood of bones grinding together and causing discomfort. Hyaluronic acid is extremely effective at relieving joint discomfort and improving flexibility.

Type II collagen has a significant effect on reducing swelling, discomfort, and degradation in joints. It aids in connective tissue health, as well as improves discomfort, mobility, and ease of motion for people with joint conditions. Similarly, natural eggshell membrane can treat pain and inflexibility associated with joint and connective tissue disorders.

Cat's Claw is a vine from the basin of the Amazon River. Two species, *U. tomentosa* and *U. guianensis* have anti-inflammatory properties. Curcumin can downregulate the catabolic and degradative effects in cartilage explants or chondrocytes. Cayenne pepper can help treat circulatory problems and is considered as a "central circulatory stimulant." It is believed that the ability of cayenne to cleanse the whole body and help improve health conditions, such as arthritis, is due to a substance known as capsaicin.

Willow bark's pain-relieving and anti-inflammatory activity is associated with down regulation of the inflammatory mediators tumor necrosis factor-a and nuclear factor-kappa B. Moreover, its active ingredient, salicin, reduces the production of pain-inducing chemicals in nerves. Evidence suggests that willow bark may have a moderate to significant effect in treating pain caused by osteoarthritis and rheumatoid arthritis.

While each of the above ingredients has its own beneficial and powerful properties, combined, the ingredients provide an even more effective and powerful matrix for the treatment of osteoarthritis and joint pain/stiffness.

Example: Patient Trial

A patient trial for the formulation of the present disclosure was completed, wherein the study took 3 months to finish, and included 50 volunteers at three separate locations in the United States. All patients in the study were over 18 and had moderate to severe joint pain and/or discomfort at the start of the trial.

The study required that all patients assess their current pain levels prior to use of the formulation of the present disclosure, using a supplied Patient Assessment Form. In the assessment, the patients were asked to localize their pain to specific areas of their body and to also provide background on injury dates, treatments, surgeries, and any current or past medications. This provided a baseline from which results could be measured. Patients were also requested to discontinue use of any and all supplements prior to use of the formulation of the present disclosure. All patients took two capsules of the formulation per day for 30 days.

During the study, patients stopped any pain medicine they had been taking, and started taking 1360 mg (two capsules) of the formulation of the present disclosure every day. Patients were asked to keep a detailed pain diary and rate pain from 0 (no pain) to 10 (extreme pain) every day. The pain scale was defined as follows: 0 (no pain), 1-4 (mild pain), 4-7 (moderate pain), and 7-10 (severe pain).

If a patient's pain was not at least 30% lower on the pain scale after 2 weeks, or if the patient experienced GI pain or discomfort, the patient stopped taking the formulation and left the stud.

The results of the study showed that the formulation of the present disclosure had a significant impact on reducing joint discomfort and stiffness for most patients. The patient group with the most dramatic change had an initial reported pain level of 8 being reduced to 1 after 5 weeks, with two a day dosage. This represented a pain reduction of 80% over the baseline of the trial. For all patient groups, a median of 7 was the baseline, with a median of 2 at the conclusion of the trial. This represented a median improvement of 72% in aggregate. The patient group with the least pain reduction still had a reduction of 67% from the baseline. No group reported pain stasis or increase, and all groups reported pain reduction and mobility gains of some level.

Most patients who finished the study felt dramatically better than when they started. Patients had less joint pain, stiffness, and discomfort. Many patients also reported the resumption of physical activities that they had abandoned and also said their daily activities were easier to complete because moving was easier. An unanticipated result is that a number of patients reported skin appearance improvements, as well as the disappearance of significant skin blemishes and, in some cases, warts and other dermatological conditions.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A nutraceutical dietary supplement formulation for the treatment of joint pain and discomfort, the formulation comprising:
   astaxanthin powder;
   *Boswellia serrata* gum resin extract;
   hyaluronic acid;
   undenatured type II (UC-II) collagen;
   eggshell membrane collagen powder;
   turmeric root extract;
   white willow bark extract;
   cayenne pepper extract; and
   Cat's Claw bark powder.

2. The formulation of claim 1, wherein the eggshell membrane collagen powder comprises type IV eggshell collagen.

3. The formulation of claim 1, wherein the turmeric root extract comprises turmeric root extract 95% curcuminoids.

4. The formulation of claim 1, wherein a batch comprises:
   about 1 to about 6 mg astaxanthin powder 2;
   about 100 to about 200 mg *Boswellia serrata* gum resin extract;
   about 30 to about 50 mg hyaluronic acid;
   about 30 to about 50 mg UC-II collagen;
   about 75 to about 125 mg eggshell membrane collagen powder;
   about 75 to about 125 mg turmeric root extract;
   about 25 to about 75 mg white willow bark extract;
   about 25 to about 75 mg cayenne extract; and
   about 75 to about 125 mg Cat's Claw bark powder.

5. The formulation of claim 1, wherein the batch comprises:
   2 mg astaxanthin powder;
   150 mg *Boswellia serrata* gum resin extract;
   42 mg hyaluronic acid;
   42 mg UC-II collagen;
   105 mg eggshell membrane collagen powder;
   104 mg turmeric root extract;
   50 mg white willow bark extract;
   50 mg cayenne extract; and
   100 mg Cat's Claw bark powder.

* * * * *